United States Patent
Bitter et al.

(10) Patent No.: US 8,558,201 B2
(45) Date of Patent: Oct. 15, 2013

(54) INFRARED RADIATOR ARRANGEMENT FOR A GAS ANALYSIS DEVICE

(75) Inventors: Ralf Bitter, Karlsruhe (DE); Camiel Heffels, Stutensee-Büchig (DE); Thomas Hörner, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 143 days.

(21) Appl. No.: 13/256,194

(22) PCT Filed: Mar. 13, 2010

(86) PCT No.: PCT/EP2010/053237
§ 371 (c)(1),
(2), (4) Date: Nov. 22, 2011

(87) PCT Pub. No.: WO2010/103123
PCT Pub. Date: Sep. 16, 2010

(65) Prior Publication Data
US 2012/0056112 A1    Mar. 8, 2012

(30) Foreign Application Priority Data
Mar. 13, 2009    (DE) .......................... 10 2009 013 096

(51) Int. Cl.
*A61N 5/06* (2006.01)
*G01J 3/10* (2006.01)
*H05G 2/00* (2006.01)
*H05B 3/20* (2006.01)

(52) U.S. Cl.
USPC ................. 250/504 R; 250/338.1; 250/339.1; 250/341.1; 250/493.1; 392/434; 392/438; 392/309; 219/553; 219/548; 219/411; 219/538; 219/540; 338/18; 338/293; 338/308

(58) Field of Classification Search
USPC ........... 250/336.1, 338.1, 339.06, 340, 341.1, 250/363.01, 492.1, 493.1, 494.1, 495.1, 250/504 R; 392/309, 407, 434, 435, 437, 392/438, 439; 219/411, 436, 536–540, 542, 219/543, 548, 551–553; 338/17, 18, 292, 338/293, 300, 301, 308, 309
See application file for complete search history.

(56) References Cited

U.S. PATENT DOCUMENTS

| | | |
|---|---|---|
| 3,694,624 A | 9/1972 | Buchta |
| 3,875,413 A | 4/1975 | Bridgham |
| 4,620,104 A | 10/1986 | Nordal et al. |
| 4,644,141 A | 2/1987 | Hagen et al. |

(Continued)

FOREIGN PATENT DOCUMENTS

| | | |
|---|---|---|
| CN | 1849500 | 10/2006 |
| DE | 1936245 | 2/1971 |

(Continued)

*Primary Examiner* — Bernard E Souw
(74) *Attorney, Agent, or Firm* — Cozen O'Connor

(57) ABSTRACT

A method and device for measuring the soot load in the exhaust gas systems of diesel engines using a sensor which is mounted downstream of a particulate filter and comprises a sensor element, to measure the operability of the particulate filter. According to the method, the soot load of the sensor element is measured resistively or capacitively using electrodes. The measuring voltage of the sensor element is controlled depending on at least one actual operating parameter of the diesel engine.

8 Claims, 3 Drawing Sheets

(56) References Cited

U.S. PATENT DOCUMENTS

| | | | |
|---|---|---|---|
| 5,436,457 | A | 7/1995 | Tomita |
| 5,602,398 | A | 2/1997 | Knodle et al. |
| 6,249,005 | B1 | 6/2001 | Johnson |
| 6,452,137 | B1 * | 9/2002 | Kariya .......................... 219/544 |
| 6,591,062 | B2 | 7/2003 | Scherzer et al. |
| 7,378,656 | B2 | 5/2008 | Ichihara et al. |
| 7,947,933 | B2 * | 5/2011 | Nagasako et al. ............. 219/544 |
| 7,982,166 | B2 * | 7/2011 | Kukino et al. ................ 219/542 |
| 8,115,139 | B2 | 2/2012 | Scharf et al. |
| 2005/0133495 | A1 * | 6/2005 | Kariya .......................... 219/552 |

FOREIGN PATENT DOCUMENTS

| | | |
|---|---|---|
| DE | 2442892 | 4/1975 |
| DE | 4420340 | 12/1994 |
| DE | 10029437 | 1/2002 |
| DE | 102004035014 | 2/2006 |
| EP | 0177724 | 4/1986 |
| EP | 1168418 | 1/2002 |
| EP | 1679735 | 7/2006 |
| JP | 9153640 | 6/1997 |
| WO | WO 9706417 | 2/1997 |

* cited by examiner

INFRARED RADIATOR ARRANGEMENT FOR A GAS ANALYSIS DEVICE

CROSS-REFERENCE TO RELATED APPLICATIONS

This is a U.S. national stage of International Application No. PCT/EP2010/053237, filed on 13 Mar. 2010. This patent application claims the priority of German Patent Application No. 10 2009 013 096.9, filed 13 Mar. 2009, the content of which is incorporated herein by reference its entirety.

BACKGROUND OF THE INVENTION

1. Field of the Invention

The invention relates to an infrared radiator arrangement for a gas analysis device including a radiator housing, a plate-shaped ceramic body arranged in the interior of the radiator housing and a structured heat resistant layer applied on the plate-shaped ceramic body housing and, where the interior of the radiation housing is closed off on one side by a radiation-transmissive window.

2. Description of the Related Art

Resistance radiators are usually used as broadband radiation source for infrared gas analysis, where a coiled filament is arranged in a reflector housing that is closed off by a radiation-transmissive window, e.g., a $CaF_2$-IR window. Here, the housing is filled with a protective gas, e.g., $N_2$, in order to avoid chemical reactions between the coiled filament and the surrounding air. However, it is also possible to use different gases, e.g., $O_2$, in order to produce a protective layer, e.g., an oxide layer, on the coiled filament.

Planar radiation sources are known, where a structured heat resistant layer using a thick or thin film technique is formed directly on a radiation-transmissive window (e.g., U.S. Pat. No. 4,620,104) or on a ceramic body arranged in a radiator housing (e.g., DE1936245, DE4420340).

In the arrangement disclosed in DE1936245, a heat resistant layer is deposited on the front side of a rectangular ceramic platelet, on the back side of which a platinum resistance thermometer is deposited, cemented with putty, or sintered. The ceramic platelet is supported by connectors for the heat resistant layer and the platinum resistance thermometer, which lead outward through the rear wall of the radiator housing.

In the arrangement disclosed in DE4420340, a heat resistant layer using a thick film technique is printed onto the front side of a likewise rectangular AlN substrate in a snaking manner as a paste, e.g., Pt-paste, and is subsequently baked. A thermosensor comprising a thermocouple is applied on the rear side of the ceramic substrate. DE4420340 does not disclose precisely how the ceramic substrate is mounted in the radiator housing.

SUMMARY OF THE INVENTION

It is therefore an object of the invention to provide an infrared radiator arrangement in which a secure and precisely defined mount of the ceramic body with a heat resistant layer applied thereon is ensured.

This and other objects are achieved in accordance with the invention by providing a plate-shaped ceramic body that comprises an equilateral triangular plate that is mounted on the internal circumference of the radiator housing using its triangular tips. The triangular tips are not necessarily pointed, but can be rounded or flattened.

The three-point mount results in a secure and precisely defined mount of the ceramic body in the radiator housing. In the process, the triangular plate is preferably mounted at its triangular tips in a circumferential groove disposed the internal circumference of the radiator housing. Alternatively, a mechanism for holding the triangular tips can be created by local projections or recesses formed on the housing inner wall or by spring elements provided at this location.

A further advantage of the arrangement in accordance with the invention consists of the three-point mount minimizing the heat dissipation from the ceramic body to the radiator housing. This allows the heat resistant layer and, if present, further resistance layers that, for example, serve for temperature measurement to be connected to connection lines in the region of the triangular tips of the triangular plate by soldered connections. Alternative connection methods are, e.g., sintering or welding.

In order to improve temperature distribution, and hence the voltage distribution, within the triangular plate, particularly in the regions of the edges thereof, partial structures of the heat resistant layer are arranged along the edges of the triangular plate and in the vicinity of the triangular plate. By way of example, these partial structures may extend in a straight line, parallel to the edges, or may meander in the region between the edges and the remaining structures of the heat resistant layer in the inner region of the triangular plate.

The ceramic body is only heated on one side at its edges. As a result, heat is dissipated at the edges of the ceramic body. Therefore, the partial structures of the heat resistant layer preferably have a higher electric resistance along the edges than the remaining structures of the heat resistant layer. Consequently, stronger Ohmic heating at the edges of the ceramic body. The higher electric resistance may, for example, be realized by a reduced line cross section or by doping the heat resistant layer.

As a result of the triangular shape of the ceramic body, there are openings between the edges thereof and the inner wall of the radiator housing. In order to additionally guide radiation components originating from the side of the ceramic body facing away from the window to the window through the openings, the radiator housing can have a suitably configured reflector on its inner side lying opposite the window.

Finally, it is easy to produce the triangular ceramic body in relatively large numbers from a large-area ceramic substrate by deliberately introducing break lines into the ceramic substrate by scratching or laser perforation along parallel lines in three directions, respectively rotated with respect to one another by 60°, along which intended break lines the individual ceramic bodies are singled out by breaking. The edges of the triangular plate are then breaking edges.

The resistance of the heat resistant layer or further heat resistant layers can be measured in a known manner for measuring and regulating the temperature. However, age-related changes in the resistance may lead to different temperatures and hence to different intensity spectra of the generated radiation despite closed-loop control to an unchanging resistance value. Such age-related changes in the heat resistant layer can be detected by a redundant temperature acquisition using at least two resistor structures with different temperature properties. By way of example, the different temperature property can be set by appropriate doping of the resistance layer.

Other objects and features of the present invention will become apparent from the following detailed description considered in conjunction with the accompanying drawings. It is to be understood, however, that the drawings are designed solely for purposes of illustration and not as a definition of the limits of the invention. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the following text, reference is made to the figures in the drawings for the further explanation of the invention, in which.

DETAILED DESCRIPTION OF THE PREFERRED EMBODIMENTS

Figure 1:
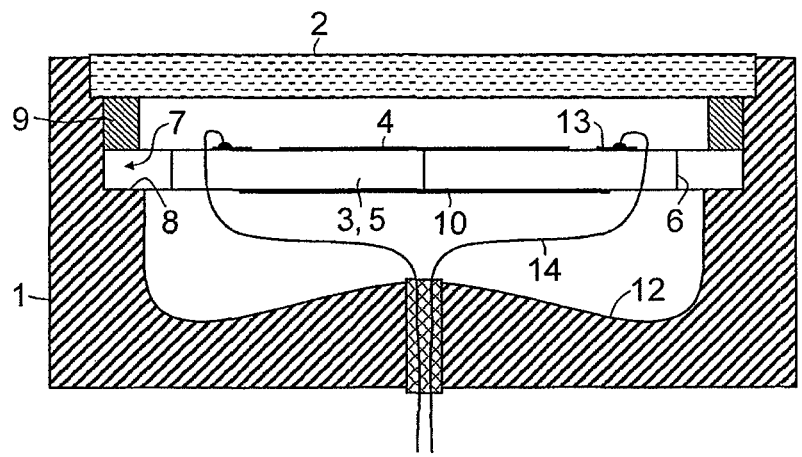
FIG. 1 is a cross sectional illustration of an exemplary embodiment of the infrared radiator arrangement with a ceramic body supporting a heat resistant layer, in accordance with the invention.

FIG. 1 shows a cross section of an infrared radiator arrangement with a radiator housing 1, the interior of which is closed off by an infrared-transmissive window 2. Arranged in the radiator housing 1 is a plate-shaped ceramic body 3, where a structured heat resistant layer 4 is shown applied on the side of the plate-shaped ceramic body 3 facing the window.

Figure 2:
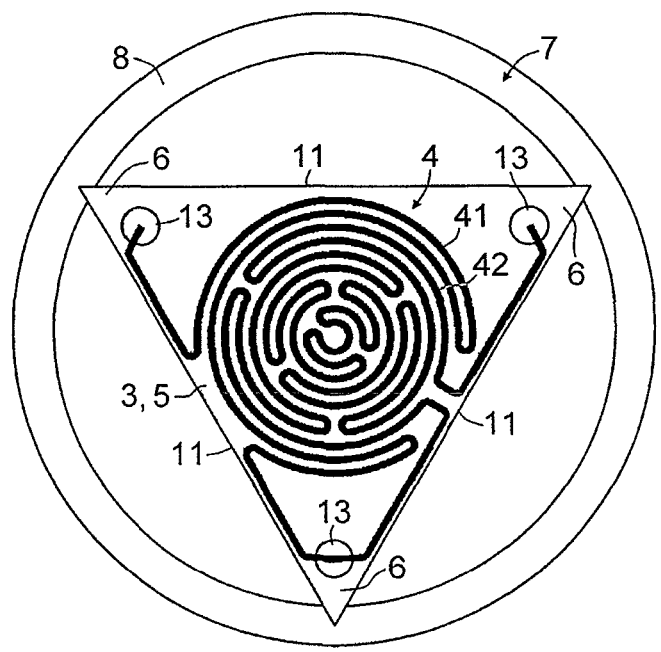
FIG. 2 is a plan view illustration of the ceramic body.

FIG. 2 shows a plan view of the plate-shaped ceramic body 3 comprising an equilateral triangular plate 5 mounted at its triangular tips 6 in a circumferential groove 7 arranged in the inner circumference of the radiator housing 1. The groove 7 is formed by a circumferential shoulder 8, situated in the radiator housing 1, and a clamping collar 9 arranged between the window 2 and the ceramic body 3. A heat resistant layer 4 consists of a platinum paste, which is applied to the ceramic body 3 by screen printing and subsequently baked. It is possible to print a plurality of heating structures 41, 42 or structures for temperature acquisition on one or both sides of the ceramic body 3. FIG. 2 shows two snake-like heating structures, electrically connected in series, which can each be heated independently and therefore can both be used for temperature measurement and hence for temperature regulation. Alternatively or additionally, a platinum structure 10 can be applied to the rear side of the ceramic body 3 for (redundant) temperature measurement.

The triangular shape ensures a stable mount of the ceramic body 3 in the radiator housing 1. Furthermore, there are openings between the edges 11 of the ceramic body 3 and the inner wall of the radiator housing 1 as a result of the triangular shape, through which openings the radiation components originating from the side of the ceramic body 3 facing away from the window 2 are routed to the window 2 by a reflector 12.

As a result of the three-point mount, the heat dissipation from the ceramic body 3 to the radiator housing 1 is minimized. As a result, it is possible, in the region of the triangular tips 6 of the triangular plate 5, to connect the heat resistant layer 4 and further heat resistant layers 10 to contact areas 13 by soldered connections with connection lines 14, which are routed out of the radiator housing 1 on the rear side thereof.

Figure 3:
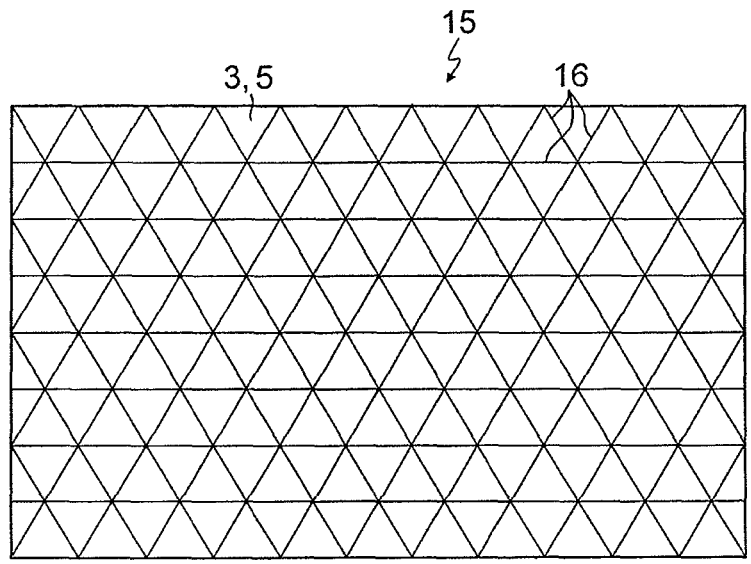
FIG. 3 is a schematic illustration of an exemplary ceramic substrate with intended break lines for separating a multiplicity of ceramic bodies.

FIG. 3 shows a large-area ceramic substrate 15, from which the triangular ceramic body 3 can easily be produced in relatively large numbers. To this end, intended break lines are introduced into the ceramic substrate 15 by scratching or laser perforation along parallel lines 16 in three directions, respectively rotated with respect to one another by 60°, along which intended break lines the individual ceramic bodies 3 are singled out by breaking. The edges 11 of the triangular plate 5 are then breaking edges (see, e.g., FIG. 2).

Figure 4:
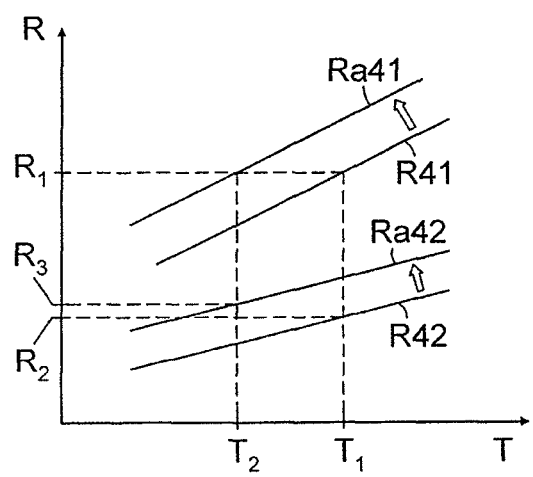
FIG. 4 is an exemplary graphical plot of the resistance/temperature characteristics of two resistor structures with different temperature properties.

FIG. 4 shows a graphical plot of the resistance/temperature (R/T) characteristics R41 and R42 of two resistor structures, in this case 41 and 42 from FIG. 2, with different temperature properties that are achieved by, e.g., doping one of the resistor structures or doping the two resistor structures differently. The characteristic R41 changes into Ra41 and the characteristic R42 changes into Ra42 as a result of aging. The resistor structure 41 is heated to a temperature $T_1$ in a resistance-regulated manner, where the resistance setpoint value is $R_1$. The resistance value $R_2$ is measured at the resistor structure 42 at this temperature $T_1$. After aging of the resistor structures 41 and 42, the unchanging continued regulation of the resistor structure 41 to the resistance value $R_1$ leads to an undesirably reduced temperature $T_2$. However, at this temperature $T_2$, the resistor structure 42 does not measure the original resistance value $R_2$ as a result of the different temperature property but rather a modified resistance value $R_3$, which indicates an age-dependent change in the resistance of the resistor structures 41 and 42 and an incorrectly set temperature.

Figure 5:
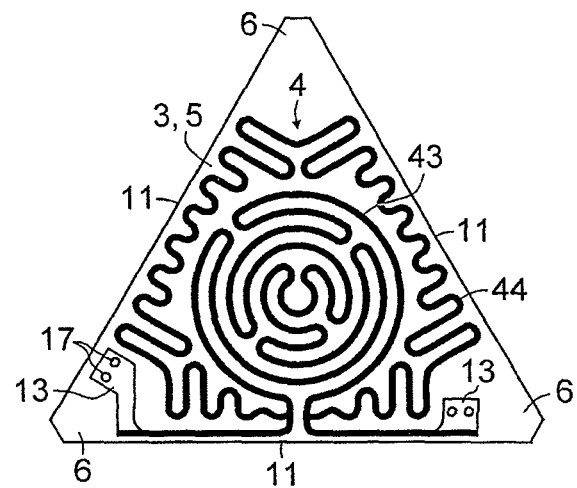
FIGS. 5 and 6 are illustrations of an exemplary ceramic body with differently structured heat resistant layers.

FIG. 5 shows the ceramic body 3 comprising the equilateral triangular plate 5 with in this case flattened triangular tips 6. The heat resistant layer 4 consists of an inner partial structure 43, similar to the heating structure 42 in FIG. 2, and an outer partial structure 44, which meanders in the regions between the edges 11 of the triangular plate 5 and the inner partial structure 43 of the heat resistant layer 4. This brings about even heating of all regions of the triangular plate 5 with the exception of the triangular tips 6.

Two small holes 17 are respectively provided in the contact surfaces 13 to connect the connection wires 14 (FIG. 1) therein before they are sintered on. As a result, a reduction is provided of the mechanical load on the sintered contact sites.

Figure 6:
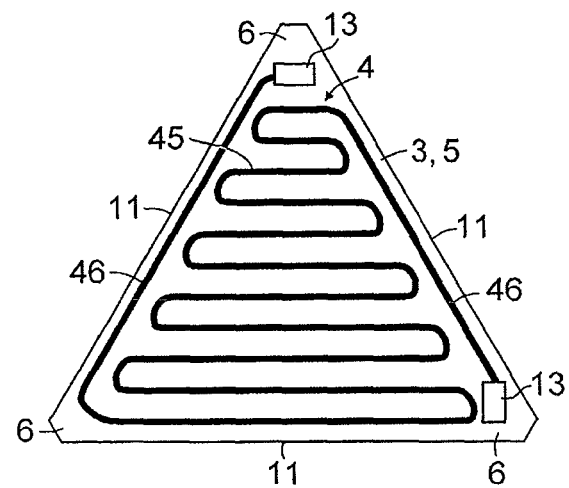

In the exemplary embodiment shown in FIG. 6, the heat resistant layer 4 comprises an inner partial structure 45, which meanders over the surface of the triangular plate 5, and an outer partial structure 46 comprising feed lines of the inner partial structure 45 that extend in a straight line parallel to the edges 11. The ceramic body 3 is only heated on one side on the edges 11 thereof. As a result, heat is dissipated at this location. It is for this reason that the outer partial structure 46 of the heat resistant layer 4 is designed to have a higher resistance than the inner partial structure 45.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice.

The invention claimed is:

1. An infrared radiator arrangement for a gas analysis device, comprising:

a radiator housing;

a plate-shaped ceramic body arranged in an interior of the radiator housing;

a structured heat resistant layer applied on the plate-shaped ceramic body;

a radiation-transmissive window arranged on one side of the radiator housing to close off the interior of the radiator housing;

wherein the plate-shaped ceramic body comprises an equilateral triangular plate mounted on an internal circumference of the radiator housing at triangular tips of the equilateral triangular plate.

2. The infrared radiator arrangement as claimed in claim 1, wherein the equilateral triangular plate is mounted at the triangular tips in a circumferential groove disposed in an internal circumference of the radiator housing.

3. The infrared radiator arrangement as claimed in claim 1, wherein the structured heat resistant layer is connected to connection lines in a region of the triangular tips of the equilateral triangular plate.

4. The infrared radiator arrangement as claimed in claim 2, wherein the structured heat resistant layer is connected to connection lines in a region of the triangular tips of the equilateral triangular plate.

5. The infrared radiator arrangement as claimed in claim 1, further comprising:

additional heat resistant layers applied on a surface of the plate-shaped ceramic body opposite to the structured heat resistant layer;

wherein the structured heat resistant layer and the additional heat resistant layers are connected to connection lines in a region of the triangular tips of the equilateral triangular plate.

6. The infrared radiator arrangement as claimed in claim 1, wherein partial structures of the structured heat resistant layer are arranged along edges of the equilateral triangular plate and in a vicinity of the equilateral triangular plate.

7. The infrared radiator arrangement as claimed in claim 6, wherein the partial structures of the structured heat resistant layer have a higher electric resistance along the edges of the equilateral triangular plate than remaining structures of the structured heat resistant layer.

8. The infrared radiator arrangement as claimed in claim 1, further comprising:

a reflector arranged on an on inner side of the radiator housing and opposite the radiation-transmissive window.

\* \* \* \* \*